United States Patent [19]
Taylor et al.

[11] Patent Number: 5,716,349
[45] Date of Patent: Feb. 10, 1998

[54] ABSORBENT ARTICLE HAVING LONGITUDINAL SIDE MARGINS WITH TUCKS

[75] Inventors: Joann Lee Taylor, Trenton; Kenneth Barclay Buell; Thomas Ward Osborn, III, both of Cincinnati, all of Ohio

[73] Assignee: The Procter & Gamble Company, Cincinnati, Ohio

[21] Appl. No.: 338,358

[22] Filed: Nov. 14, 1994

Related U.S. Application Data

[63] Continuation of Ser. No. 240,959, May 11, 1994, abandoned, which is a continuation of Ser. No. 120,710, Sep. 13, 1993, abandoned, which is a continuation of Ser. No. 882,738, May 14, 1992, abandoned, which is a continuation-in-part of Ser. No. 874,872, Apr. 28, 1992, abandoned, Ser. No. 832,246, Feb. 7, 1992, abandoned, Ser. No. 810,774, Dec. 17, 1991, abandoned, Ser. No. 769,891, Oct. 1, 1991, abandoned, Ser. No. 769,607, Oct. 1, 1991, abandoned, Ser. No. 734,405, Jun. 23, 1991, abandoned, Ser. No. 734,404, Jun. 23, 1991, abandoned, and Ser. No. 734,392, Jun. 23, 1991, abandoned.

[51] Int. Cl.⁶ ............................ A61F 13/15; A61F 13/20
[52] U.S. Cl. ............................ 604/385.1; 604/386
[58] Field of Search ............................ 604/358, 378, 604/385.1, 385.2, 386

[56] References Cited

U.S. PATENT DOCUMENTS

| | | |
|---|---|---|
| 3,744,494 | 7/1973 | Marsan ............................ 604/378 |
| 3,776,233 | 12/1973 | Schaar ............................ 604/385.1 |
| 3,807,402 | 4/1974 | Miller et al. ............................ 604/378 |
| 4,108,179 | 8/1978 | Schaar . | 
| 4,654,040 | 3/1987 | Luceri ............................ 604/385.1 |
| 4,701,177 | 10/1987 | Ellis et al. ............................ 604/385 |
| 4,731,070 | 3/1988 | Koci ............................ 604/385.1 |
| 4,758,241 | 7/1988 | Papajohn ............................ 604/387 |
| 4,770,657 | 9/1988 | Ellis et al. ............................ 604/385 |
| 4,772,282 | 9/1988 | Oakley ............................ 604/385.1 |
| 4,790,838 | 12/1988 | Pigneul et al. ............................ 604/385.1 |
| 4,941,933 | 7/1990 | Korpman ............................ 604/385.1 |
| 4,944,735 | 7/1990 | Mokry ............................ 604/385.2 |
| 5,032,121 | 7/1991 | Mokry ............................ 604/385.2 |
| 5,181,563 | 1/1993 | Amaral ............................ 604/385.2 |

FOREIGN PATENT DOCUMENTS

2 168 253 A  6/1986  United Kingdom .

*Primary Examiner*—Randy C. Shay
*Attorney, Agent, or Firm*—Edward J. Milbrada; Jeffrey V. Bamber; Steven W. Miller

[57] ABSTRACT

An absorbent article, such as a sanitary napkin, having longitudinal side margins with pleats or tucks is provided. The tucks cause the absorbent article to assume a curved, body-conforming shape, and provide the absorbent article with sides that stand up to serve as a barrier to soiling of the wearer's undergarments.

4 Claims, 4 Drawing Sheets

ABSORBENT ARTICLE HAVING LONGITUDINAL SIDE MARGINS WITH TUCKS

CROSS-REFERENCE TO RELATED APPLICATIONS

This is a continuation of Ser. No. 240,759 filed May 11, 1994, now abandoned, which is a continuation of Ser. No. 120,710 filed Sep. 13, 1993, now abandoned, which is a continuation of Ser. No. 882,738 filed May 14, 1992, which is a continuation-in-part of the following U.S. patent applications: Ser. Nos. 07/734,392, 07/734,404, and 07/734,405 filed Jul. 23, 1991, and all now abandoned; Ser. Nos. 07/769,607 and 07/769,891 filed Oct. 1, 1991, and both now abandoned; and Ser. No. 07/810,774 filed Dec. 17, 1991, now abandoned; Ser. No. 07/832,246 filed Feb. 7, 1992 now abandoned; and Ser. No. 07/874,872 filed Apr. 28, 1992, now abandoned.

FIELD OF THE INVENTION

The present invention relates to absorbent articles such as sanitary napkins, panty liners, adult incontinence devices, and the like. More particularly, the present invention concerns absorbent articles having longitudinal side margins with pleats or tucks. The tucks cause the absorbent articles to assume a curved, body-conforming shape, and provide the absorbent article with sides that stand up to serve as a barrier to soiling of the wearer's undergarments.

BACKGROUND OF THE INVENTION

All manner and variety of absorbent articles configured for the absorption of body fluids such as menses, urine, and feces are, of course, well known.

Generally, absorbent articles are configured so that they have a longitudinal dimension and transverse dimension, the latter being smaller to fit between the wearer's legs in the area of the wearer's crotch. One persistent problem with absorbent articles is that the forces applied by the wearer's legs during use tend to compress and distort the absorbent articles making them unable to conform to the wearer's body. Another problem is the tendency for leakage to occur along the longitudinal side edges of the absorbent articles. The causes of such leakage can be attributed to a number of factors. These include the fact that liquids simply have a shorter distance to travel to reach the longitudinal side edges. The compression and distortion of the sanitary napkin also contribute to side leakage.

While work has progressed in attempting to create absorbent articles that conform to the wearer's body and to solve such longitudinal side leakage in various different types of absorbent articles, a good deal of the most recent work has been done with sanitary napkins. Currently, the trend has been to provide sanitary napkins with elasticized longitudinal side edges.

Sanitary napkins provided with elastics of various types are disclosed in European Patent Application Publication No. 0 091 412 A2 published Oct. 12, 1983, P&G U.K. Patent Application 2 168 253 A published Jun. 18, 1986 (which also discloses means for holding the side flaps therein in an upwardly folded configuration other than elastics), and U.S. Pat. No. 4,701,177 issued to Ellis, et al. on Oct. 20, 1987, U.S. Pat. No. 4,758,241 issued to Papajohn on Jul. 19, 1988, U.S. Pat. No. 4,770,657 issued to Ellis, et al. on Sep. 13, 1988, U.S. Pat. No. 4,944,735 issued to Mokry on Jul. 31, 1990, and U.S. Pat. No. 5,032,121 issued to Mokry on Jul. 16, 1991. The disclosures of all these documents are incorporated by reference herein.

There are a number of problems with using elastics for the above purposes. The addition of elastics increases the cost of producing sanitary napkins. The attachment of elastic strands to a moving web during the manufacturing of sanitary napkins is a fairly complicated and expensive process. Another problem is that the use of elastics for the purpose of causing a sanitary napkin to assume a curved shape is dependent on the thickness of the sanitary napkin. It is more difficult to achieve curvature in sanitary napkins having relatively thick absorbent means using elastics. Further, using elastics in thick products creates stresses in the elastics which resist the effort to impart curvature to the sanitary napkin. These stresses also tend to cause the elastics to lose their modulus of elasticity. The use of elastics also adds significant thickness to the product's longitudinal side barriers. This often results in a sanitary napkin that is less comfortable for the wearer.

One alternative to providing sanitary napkins with elastics along their longitudinal edges is described in U.S. Pat. No. 4,772,282 issued to Oakley on Sep. 20, 1988. The Oakley patent discloses a sanitary napkin with drawstrings located inside flaps that run along the longitudinal edges of the sanitary napkin. The use of drawstrings, however, also suffers from the disadvantage that it requires the attachment of an additional component to the sanitary napkin.

Therefore, it is an object of the present invention to provide an absorbent article, such as a sanitary napkin, with a curved shape and longitudinal side margins that form stand-up barriers without attaching elastics to the longitudinal side edges of the absorbent article.

It is another object of the invention to provide an absorbent article with a curved configuration by a means that is not affected by the thickness of the absorbent article.

It is another object of the present invention to provide an absorbent article with stand-up barriers by a means that does not significantly add to the thickness of the longitudinal side edges of the absorbent article.

It is an another object of the present invention to provide an absorbent article with such properties which is less expensive to make than absorbent articles which have elastics on their longitudinal side edges.

These and other objects of the present invention will be more readily apparent when considered in reference to the following description and when taken in conjunction with the accompanying drawings.

SUMMARY OF THE INVENTION

In accordance with the present invention, an absorbent article, such as a sanitary napkin, having longitudinal side margins with pleats or tucks is provided. The tucks cause the absorbent article to assume a curved, body-conforming shape, and provide the absorbent article with sides that stand up to serve as a barrier to soiling of the wearer's undergarments.

The absorbent article has a first end region, a second end region, a central region between the first and second end regions, two longitudinal edges and two transverse edges. The absorbent article comprises a liquid pervious topsheet, a liquid impervious backsheet joined to the topsheet, and an absorbent core positioned between the topsheet and the backsheet. At least one, and preferably both of the longitudinal side margins of the absorbent article has at least one tuck formed therein.

The absorbent article of the present invention may also be comprised of (longitudinally and/or laterally) extensible components to provide an extensible absorbent article having tucks in its longitudinal side margins.

The present invention also provides a method of making an absorbent article having longitudinal side margins with tucks therein.

DETAILED DESCRIPTION OF THE INVENTION

Figure 1:
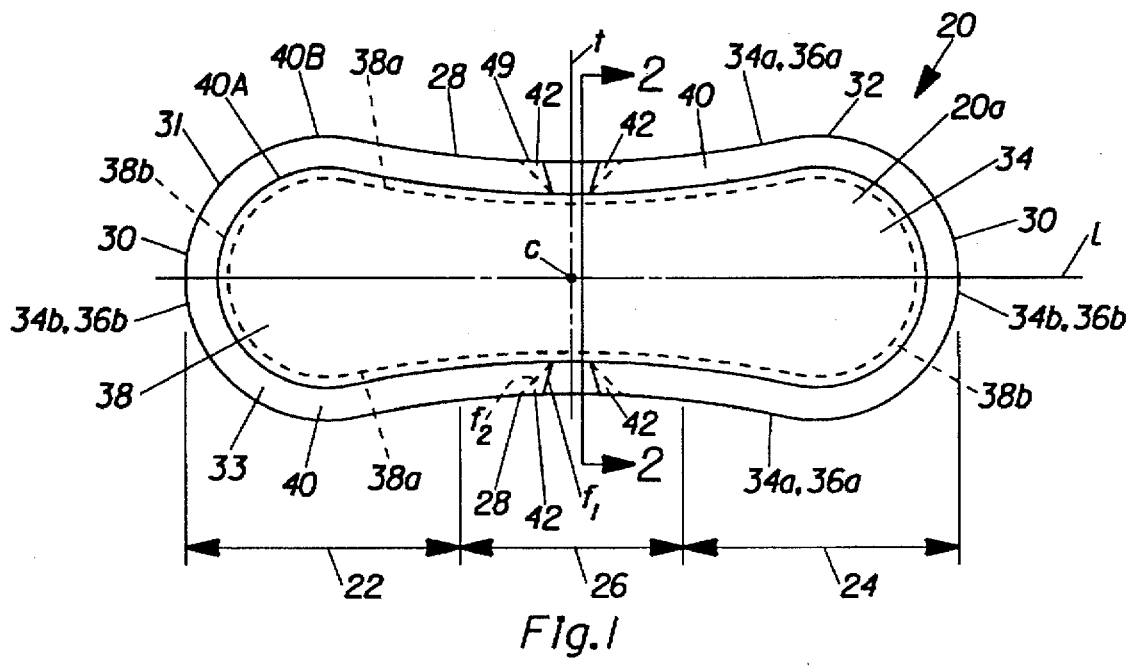
FIG. 1 is a top plan view of a preferred sanitary napkin embodiment of the present invention.

The present invention relates to absorbent articles, such as sanitary napkins, panty liners, incontinence devices, and the like. More particularly, the present invention relates to absorbent articles having longitudinal side margins with pleats or tucks. The tucks cause the absorbent article to assume a curved, body-conforming shape, and provide the absorbent article with sides that stand up to serve as a barrier to soiling of the wearer's undergarments.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, incontinent pads and other articles worn in the crotch region of a garment. The term "disposable" refers to articles which are intended to be discarded after a single use and preferably recycled, composted, or otherwise disposed of in an environmentally compatible manner. (That is, disposable articles are not intended to be laundered or otherwise restored or reused as an absorbent article.) In the preferred embodiment illustrated, the absorbent article is a sanitary napkin designated 20.

The term "sanitary napkin", as used herein, refers to an article which is worn by females adjacent to the pudendal region that is intended to absorb and contain the various exudates which are discharged from the body (e.g., blood, menses, and urine). The present invention, however, is not limited to the particular type or configuration of the absorbent article shown in the drawings.

FIG. 1 shows that the sanitary napkin 20 has a first end region 22, a second end region 24, a central or "crotch" region 26 between the first and second end regions (the terms "central region" and "end regions" are defined in U.S. Pat. No. 4,690,680 issued to Higgins on Sep. 1, 1987). The sanitary napkin 20 has two centerlines, a longitudinal centerline 1 and a transverse centerline t. The sanitary napkin 20 has two spaced apart longitudinal or side edges 28 and two spaced apart transverse or end edges (or "ends") 30 which together form the periphery 32 of the sanitary napkin.

The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" are synonymous, and refer to the line, axis or direction generally perpendicular to the longitudinal direction which lies within the plane of the sanitary napkin 20.

Figure 2:
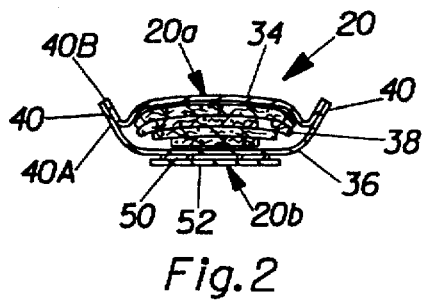
FIG. 2 is a lateral cross-sectional view of the preferred sanitary napkin embodiment shown in FIG. 1 taken along line 2—2 of FIG. 1.

FIG. 2 is a cross-sectional view of sanitary napkin 20 taken along line 2—2 of FIG. 1 which illustrates a generally preferred construction for the sanitary napkin 20. As shown in FIG. 2, the sanitary napkin 20 has a body surface 20a and a garment surface 20b. The sanitary napkin 20 is basically comprised of a topsheet 34, a backsheet 36, and an absorbent core 38. The topsheet 34, backsheet 36, and absorbent core 38 each have their own spaced apart longitudinal or side edges and transverse or end edges. (For convenience, the longitudinal and transverse edges of these components will be designated by the same reference number used for the respective component plus the letter "a" for longitudinal edges, and the letter "b" for transverse edges.)

The sanitary napkin 20 (as shown in FIGS. 1–5), is an example of a relatively thick product. In other alternative embodiments, the sanitary napkin 20 can be relatively thin, (a caliper of less than or equal to about 4 or 5 millimeters). The sanitary napkin 20 can also be an "ultra-thin" sanitary napkin (a caliper of less than or equal to about 3 mm.) such as those described in U.S. Pat. Nos. 4,950,264 and 5,009,653 issued to Osborn on Aug. 21, 1990 and Apr. 23, 1991.

Figure 3:
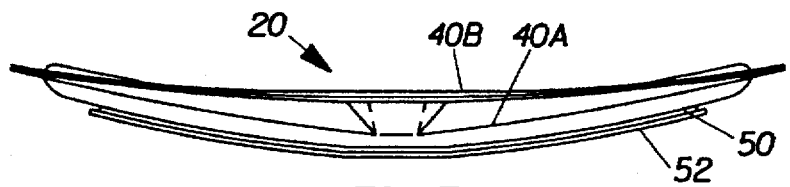
FIG. 3 is a side view of the sanitary napkin shown in FIG. 1.
Figure 4:
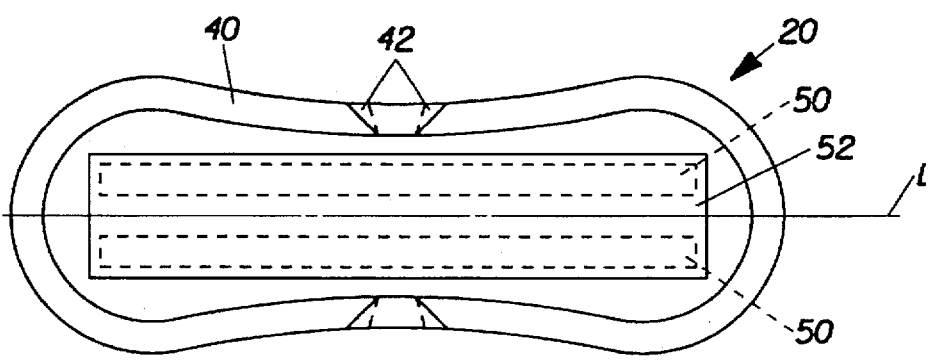
FIG. 4 is a bottom plan view of the sanitary napkin shown in FIG. 1.

The sanitary napkin 20 may be of relatively uniform thickness. Alternatively, as shown in FIGS. 1–3, the sanitary napkin can be profiled so that the thickness varies. The thickness can vary in any known manner.

The sanitary napkin as shown in FIGS. 2 and 3, is thickest in the center and is "profiled" toward the side edges 28 and end edges 30. The profiled shape is created by stacking at least one relatively wide and long layer of absorbent core material on top of at least one, and preferably more layers of lesser length and/or width. Any other suitable or known method of profiling, such as stacking the smaller layers on top, using a profiled core mold or form, calendering, etc. can also be used to create a profiled sanitary napkin.

FIG. 1 shows an embodiment in which the longitudinal edges 34a and 36a of the topsheet 34 and backsheet 36 extend outward beyond the longitudinal edges 38a of the absorbent core. The extension of these edges forms longitudinal side margins (or flanges) 40 along the longitudinal edges 28 of the sanitary napkin 20. The longitudinal side margins 40 extend from proximal edges 40A outward to distal edges 40B. (The term "outward", as used herein, means in a direction away from the intersection of the longitudinal and transverse centerlines.)

The width of the longitudinal side margins 40 is preferably between about ¼ inch (about 0.6 cm.) and about ⅜ inch (about 1 cm.), and most preferably is about ½ inch (about 1.3 cm.), although the width can be greater or less as long as the longitudinal side margins 40 provide at least some of the benefits described herein.

The longitudinal side margins 40 are preferably integral with at least the backsheet and/or topsheet. In other embodiments, however, the longitudinal side margins 40 can be formed by separate elements attached to at least one of the other components of the sanitary napkin. In still other embodiments, the longitudinal edges 38a of the absorbent core 38 can extend outward to form at least part of the longitudinal side margins 40. The longitudinal side margins 40 may, thus, be formed by the longitudinal edges of the backsheet and/or the longitudinal edges of at least one of the topsheet and the absorbent core. Forming the longitudinal side margins 40 with the longitudinal edges 36a of the backsheet 36 provides the absorbent articles with stand-up barriers that are liquid impervious.

The longitudinal side margins 40, or at least the distal edges 40B of the longitudinal side margins 40, are foreshortened (or shortened). The sanitary napkin 20 shown in FIGS. 1–4 has longitudinal side margins 40 with tucks 42 formed therein. Preferably, however, as shown in the preferred embodiment described herein, the tucks 42 do not extend inward to the core 38, although in other embodiments, they may.

The tucks 42 are formed by folding at least one portion, such as first portion 44, of the longitudinal side margin 40 (shown in FIG. 7) over or adjacent to (e.g., in a side-by-side relationship) at least one other portion of the longitudinal side margin, such as second portion 46, and securing the two portions, 44 and 46, together to prevent them from unfolding. The folding creates at least one fold line per tuck.

Figure 5:
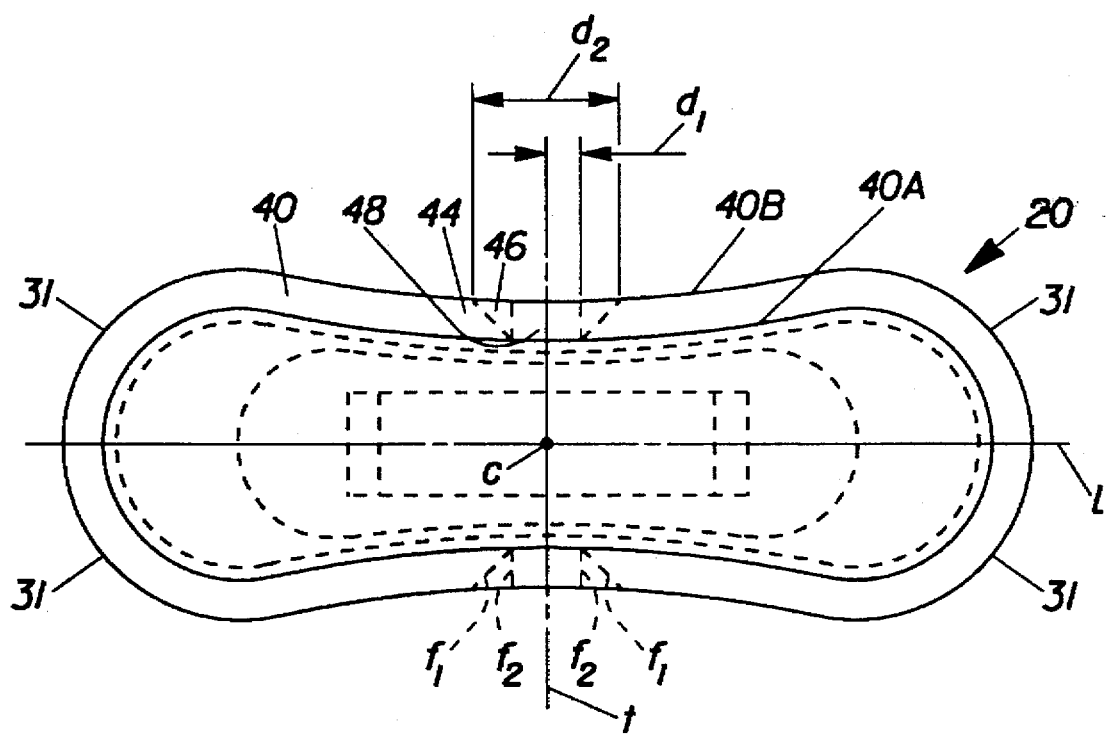
FIG. 5 is a simplified top plan view of the sanitary napkin shown in FIGS. 1–4 shown with the pleats unfolded.

FIG. 5 is a view of the sanitary napkin 20 of FIGS. 1–4 with the tucks in an unfolded condition. The longitudinal side margins 40 in the embodiment shown in FIG. 5 will have tucks 42 formed by folding the first portions 44 of the longitudinal side margin over the second portion 46, and then folding these portions over a third portion 48. This folding produces two fold lines per tuck. These are designated first fold line $f_1$ and second fold line $f_2$.

The first fold line $f_1$ shown in FIG. 5 is outboard of the second fold line $f_2$ prior to folding. The first fold line $f_1$ is preferably oriented at an angle that is about 45° from the transverse (and longitudinal) centerline. The first fold line $f_1$ runs generally parallel to an imaginary line drawn from the intersection of the longitudinal and transverse centerlines, center point c, toward one of the corners 31 of the sanitary napkin. The first fold line $f_1$ can, however, be oriented at any suitable angle to the transverse centerline t. The first fold line $f_1$ is preferably oriented at an angle up to about 90° from the transverse centerline t.

The second fold line $f_2$ runs generally parallel to the transverse centerline t. The second fold line $f_2$ is spaced about ¼ inch (about 0.6 cm.) from the transverse centerline (distance $d_1$). The spacing between the two tucks 42 on the same longitudinal side margin 40 is such that the total distance $d_2$, between the places where each of the first fold lines $f_1$ intersects with the distal edge 40B of the longitudinal side margin 40 of the sanitary napkin is about 1¼ inch (about 3 cm.).

The folding causes the first fold line $f_1$ to cross over the second fold line $f_2$ (or vice versa). The folded portions of the longitudinal side margins, 44, 46 and 48, are then secured together. The folded portions can be secured by any suitable tuck restraint (or securement means) 49. Some non-limiting examples of suitable tuck restraints 49 include thermal bonds, adhesive bonds, and ultrasonic bonds.

The characteristics of the tucks 42 can be varied to impart the desired amount of curvature to the sanitary napkin 20 (and to cause the longitudinal side margins 40 to stand up a desired amount). The sanitary napkin is preferably curved so that when the sanitary napkin is placed with one of the end regions on a flat surface, the other end region forms an angle of about 30° with respect to the plane of the flat surface. To accomplish this, the distal edges 40B of the sanitary napkin can be shortened by about 5–10%. The tucks 42 can be varied to produce the amount of curvature provided by any of the sanitary napkins that use elastics for this purpose described in the documents incorporated by reference herein in the "Background of the Invention" section.

The characteristics of the tucks 42 include the number of tucks, the width of the material folded to form the tucks, the number of folds in each tuck, the location and spacing of the tucks, and the angle of the fold lines used to form the tucks.

The sanitary napkin 20 should have at least one tuck 42 in each longitudinal side margin 40. The sanitary napkin 20 can, however, have any number of tucks 42. Typically, there will be an equal number of tucks 42 in each longitudinal side margin 40 so the curvature of the sanitary napkin is symmetrical. FIGS. 1–4 show a preferred embodiment of the sanitary napkin 20 of the present invention which has two tucks 42 along each longitudinal side margin 40. The tucks 42 on each longitudinal side margin 40 are symmetrically disposed about the transverse centerline t with one tuck 42 located on each side of the transverse centerline t.

The tucks 42 are typically located in or adjacent the central region 26 of the sanitary napkin 20. For instance, the tucks 42 could be located at the border between the central region 26 and each end region 22 and 24. The tucks 42 could thus be approximately one-third the distance inward from each end edge 30. This would be advantageous if the sanitary napkin 23 was tri-folded for packaging. The tucks 42 could, however, also be located in the end regions 22 and 24. The tucks, preferably are not solely in the end regions 22 and 24, however, since such a construction may not impart the desired curvature to the sanitary napkin.

The tucks 42 along a given longitudinal side margin 40 may be symmetrically disposed about the transverse centerline t of the sanitary napkin 20 so the curvature of the sanitary napkin is symmetrical about the transverse centerline t. However, this is not a mandatory design feature, and in some cases (such as in the case of sanitary napkins that are asymmetric about the transverse centerline), it may be desirable to form the tucks 42 asymmetrically about the transverse centerline.

Figure 7:
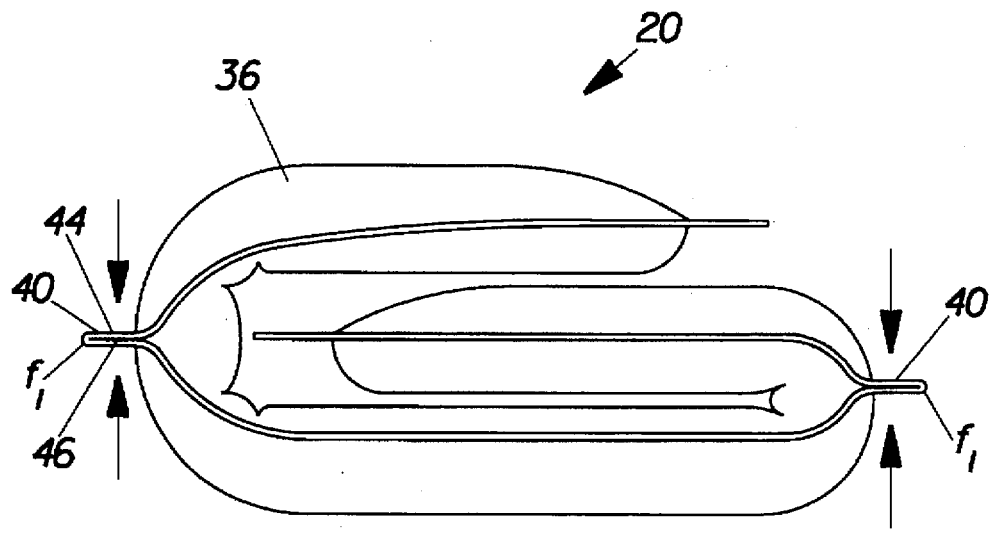
FIG. 7 is a side view showing a method of making the sanitary napkin of the present invention.
Figure 8:
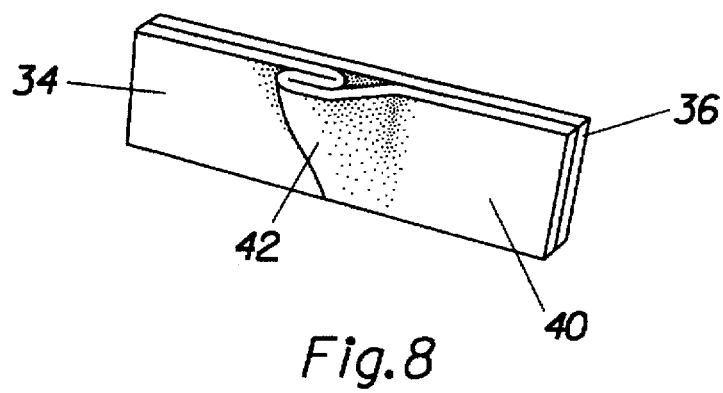
FIG. 8 is a fragmented perspective view of a portion of the longitudinal side margin of a sanitary napkin having a tuck formed in the topsheet but not the backsheet.
Figure 9:
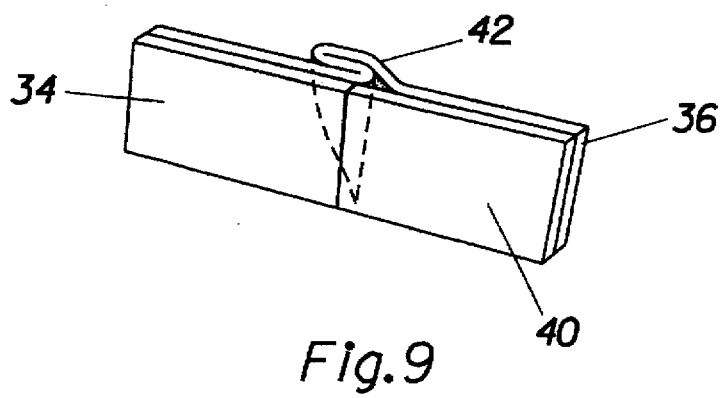
FIG. 9 is a fragmented perspective view of a portion of the longitudinal side margin of a sanitary napkin having a topsheet provided with a notch in which the material forming the edges of the notch are brought together to form a butt or lap joint, and the topsheet is joined to a backsheet having a tuck formed therein.

The longitudinal side margins 40 can be folded at any suitable stage during the manufacture of the sanitary napkin 20. Generally, as shown in FIG. 7, the tucks 42 are formed after all components, topsheet, backsheet, core, etc. are assembled. Typically, the sanitary napkin has to be bent about at least one transverse axis for the folding of the longitudinal side margins 40 to occur.

The sanitary napkin 20 can be bent a minimum amount that is merely sufficient to allow portions of the longitudinal side margins to be gathered, or the sanitary napkin 20 can be completely folded about at least one transverse axis so that the longitudinal side margins 40 overlap. In one preferred embodiment, the sanitary napkin 20 is bi-folded about a single transverse axis. In the particularly preferred embodiment shown in FIG. 7, the sanitary napkin 20 is tri-folded about two transverse axes into an "e"-folded configuration.

The individual components of the sanitary napkin 20 will now be looked at in greater detail.

The topsheet 34 is liquid permeable and, when sanitary napkin 20 is in use, in close proximity to the skin of the user. The topsheet 34 should be as compliant, soft feeling, and non-irritating to the user's skin as possible. It can be made from any of the materials conventional for this type of use. Nonlimiting examples of suitable materials that can be used as topsheet 34 are woven and nonwoven polyester, polypropylene, nylon, and rayon and formed thermoplastic films with formed films being preferred.

Suitable formed films are described in U.S. Pat. No. 3,929,135, issued to Thompson on Dec. 30, 1975, U.S. Pat. No. 4,324,426, issued to Mullane, et al. on Apr. 13, 1982, U.S. Pat. No. 4,342,314 issued to Radel, et al. and U.S. Pat. No. 4,463,045 issued to Ahr, et al. on Jul. 31, 1984. Formed films are preferred for topsheet 34 because they are pervious to liquids and, if properly apertured, have a reduced tendency to allow liquids to pass back through and rewet the wearer's skin. Thus, the surface of the formed film, which is in contact with the body, remains dry and is more comfortable to the wearer.

In some embodiments, the sanitary napkin 20 may be comprised of components that are extensible (and preferably, capable of stretching, particularly in the longitudinal direction) when the sanitary napkin is worn. Preferably, the sanitary napkin 20 is capable of elongating between about 15% and about 40% of its unstretched length. This extensibility provides better in-use fit, comfort, and decreased staining when the sanitary napkin is affixed to the wearer's undergarments.

A particularly preferred topsheet 34 for use in such an embodiment is one which is made in accordance with U.S. Pat. No. 4,463,045 and ring rolled to provide it with a degree of extensibility. One suitable process for ring rolling or "pre-corrugating" is described in U.S. Pat. No. 4,834,741 issued to Sabee on May 30, 1989. The corrugations in such a topsheet should run in the transverse direction so the topsheet is extensible in the longitudinal direction.

Such a topsheet is described in greater detail in the following patent applications which were filed on Jun. 23, 1991: U.S. patent application Ser. No. 07/734,404 filed in the names of Thompson, et al.; U.S. patent application Ser. No. 07/734,392 filed in the names of Thompson, et al.; and, U.S. patent application Ser. No. 07/734,405 filed in the names of Buenger, et al. These patent applications may be referred to collectively as the "Capillary Channel Fiber" patent applications.

In providing the sanitary napkin with such extensibility, it may be desirable for the longitudinal side margins 40 of the sanitary napkin to be less extensible or even relatively inextensible in the longitudinal direction. This will ensure that the benefits of providing the sanitary napkin with a curved shape and longitudinal side edges that form stand-up barriers obtained by shortening the distal edges 40B of the longitudinal side margins 40 will not be negated by having these edges stretch.

In addition, in preferred embodiments of the present invention, the topsheet 34 is treated with a surfactant to render the topsheet more hydrophilic. This results in liquid penetrating the topsheet 34 faster than it would if the surface were not treated. This diminishes the likelihood that menstrual fluids will flow off topsheet 34 rather than being absorbed by the absorbent core 38. This can be accomplished by any of the common techniques well known to those skilled in the art. Suitable methods for treating the topsheet with a surfactant are described in U.S. Pat. Nos. 4,950,264 and 5,009,653 issued to Osborn.

In preferred embodiments, the inner surface 34b of topsheet 34 is secured in contacting relation with an underlying absorbent layer, such as the absorbent core 38. This contacting relationship results in liquid penetrating topsheet 34 faster than if it were not in contact with absorbent core 38. The topsheet 34 can be maintained in contact with absorbent core 38 by adhesives, or by any other means known in the art. Suitable methods for applying adhesives are described in U.S. Pat. Nos. 3,911,173, 4,573,986, 4,785,996, and 4,842,666.

In alternative embodiments, the topsheet 34 can be secured to an underlying layer, such as the absorbent core 38, by fusing the topsheet 34 to the underlying layer at discrete bonded areas. Suitable absorbent articles having fused layers are described in U.S. patent application Ser. No. 07/810,774 filed in the name of Cree, et al. on Dec. 17, 1991.

Referring to FIG. 2, it can be seen that absorbent core 38 is positioned between the topsheet 34 and the backsheet 36. The absorbent core 38 provides the means for absorbing menstrual fluid. The absorbent core 38 need not have an absorbent capacity much greater than the total amount of menstrual fluid anticipated to be absorbed. Thus, the absorbent core 38 may be relatively narrow and thin. The absorbent core 38 is generally compressible, conformable, and non-irritating to the user's skin. It can comprise any material used in the art for such purpose. Examples include comminuted wood pulp which is generally referred to as airfelt, creped cellulose wadding, absorbent foams, absorbent sponges, synthetic staple fibers, polymeric fibers, hydrogel-forming polymer gelling agents, peat moss, or any equivalent material or combinations of materials.

Polymeric gelling agents are those materials which, upon contact with fluids (i.e., liquids) such as water or body fluids, imbibe such fluids and thereby form hydrogels. In this manner, fluid discharged into the absorbent core 38 can be acquired and held by the polymeric gelling agent, thereby providing the articles herein with enhanced absorbent capacity and/or improved fluid retention performance.

The polymeric gelling agent which is employed in the absorbent core 38 will generally comprise particles of a substantially water-insoluble, slightly cross-linked, partially neutralized, hydrogel-forming polymer material. The term "particles", as used herein, can refer to particles in any form, such as in the form of pellets, flakes, or fibers. The characteristics of the absorbent core 38 including, but not limited to the preferred types of polymer materials used therein, and types of methods which can be used for preparing these polymer particles, are described in greater detail in U.S. Pat. No. 5,009,653 issued to Osborn.

In one preferred embodiment, the absorbent core 38 is a laminate comprised of a layer of superabsorbent polymer material, such as in the form of particles, disposed between two air-laid tissues, first and second tissue layers (or "upper" and "lower" tissue layers). The first and second tissue layers provide containment of the superabsorbent polymer material, improve lateral wicking of the absorbed exudates throughout the absorbent core 38 and provide a degree of absorbency.

A suitable laminate is the superabsorbent laminate WATER-LOCK L-535 available from the Grain Processing Corporation of Muscatine, Iowa (WATER-LOCK registered TM by Grain Processing Corporation). Such superabsorbent laminates are disclosed in U.S. Pat. No. 4,467,012, entitled "Composition For Absorbent Film And Method Of Preparation", which issued to Pedersen et al. on Aug. 21, 1984, and U.S. Pat. No. 4,260,443, entitled "Laminated Absorbent Process", which issued to Lindsay et al. on Apr. 7, 1981.

Figure 6:
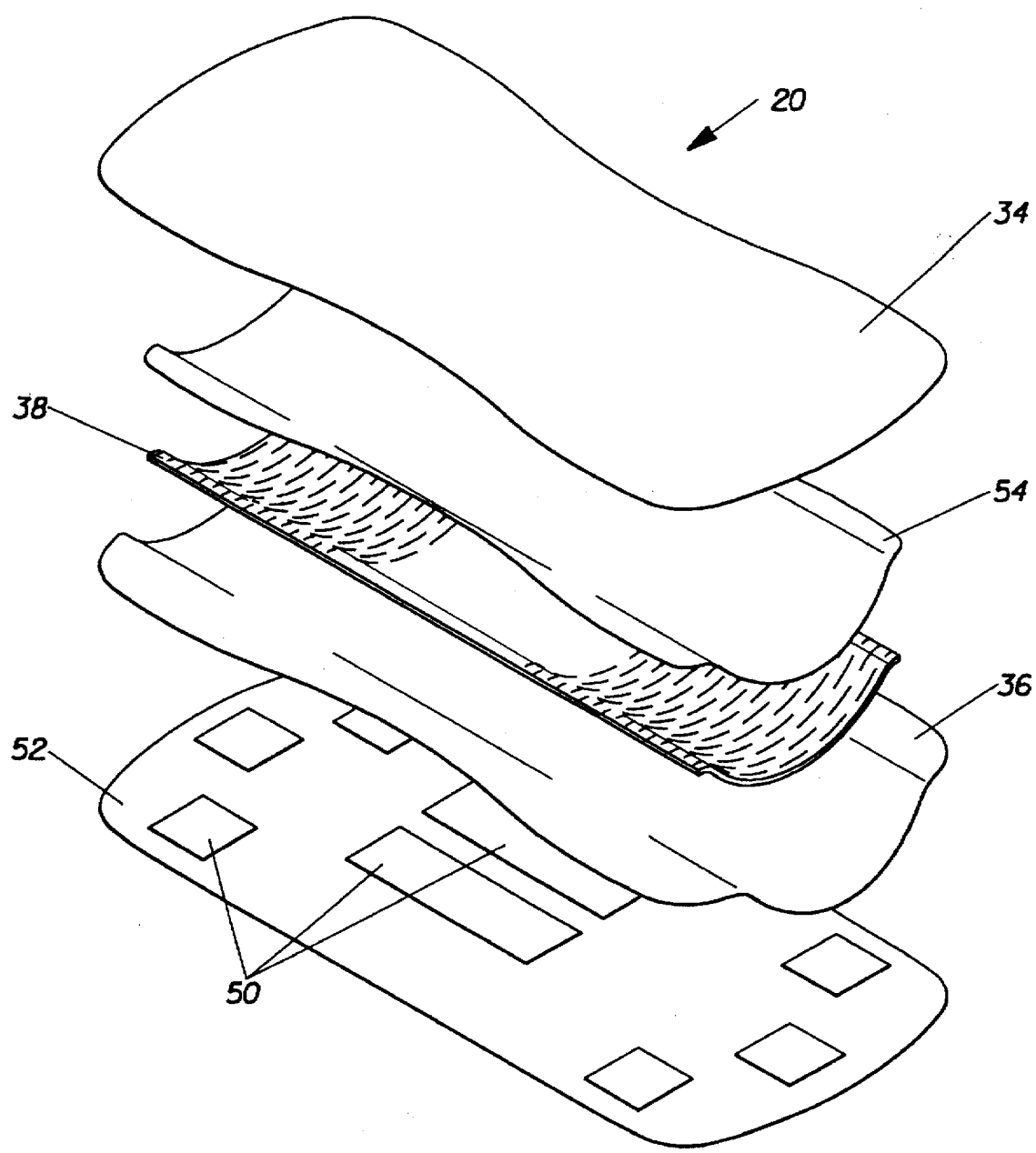
FIG. 6 is an exploded perspective view showing the assembly of a sanitary napkin which contains extensible components for use in the present invention (shown prior to providing it with tucks in its longitudinal side margins).

In a particularly preferred embodiment, the absorbent core 38 is a laminate as described above which is slitted or partially slitted for longitudinal extensibility as shown in FIG. 6 in the accompanying drawing figures. This slitted or partially slitted core is described in greater detail in the Capillary Channel Fiber patent applications.

FIGS. 1–4 show another particularly preferred absorbent core 38 that will be referred to as a "blended" core. This particular core arrangement is shown in a relatively thick sanitary napkin 20. It can, however, also be formed into a thin web for use in thin products.

The blended absorbent core 38 comprises a batt of fibers, preferably in the form of a homogeneous blend of fibers. The blended core 38 is comprised of at least two groups (or types) of fibers. These include a first group (or type) of low denier, relatively short, hydrophilic fibers, and from about 5%, preferably at least about 10 or 20% to about 90% of higher denier, longer synthetic fibers that comprise a second group (or type) of fibers. The blend ratio of the two groups of fibers can be varied to produce the properties desired for different types of absorbent articles. (All percentages specified in this description are by weight unless stated otherwise.)

The first group of fibers can comprise natural fibers such as cotton, cellulose, or other natural fibers. The first group of fibers can alternatively or additionally comprise synthetic fibers, including but not limited to, rayon, chemical thermal mechanical pulp (or "CTMP" or TMP"), ground wood, or chemically modified fibers, such as cross-linked cellulose fibers. For one embodiment, the first group of fibers comprises airfelt. The fibers in the first group of fibers are either inherently hydrophilic, or they may be rendered hydrophilic by treating them in any known manner to render them hydrophilic.

Performance is improved by selecting a relatively stiff fiber which maintains a substantial portion of its compression resistance when wetted. (That is, the fibers should have a high compressive modulus.) Preferably, the fibers selected are both compression resistant and wet and dry resilient (i.e., they tend to both resist compression and to spring back when compressed). Cross-linked cellulose fibers are especially preferred for these criteria. Suitable cross-linked cellulose fibers are described in U.S. Pat. No. 4,888,093, issued Dec. 19, 1989 to Cook, et al.; U.S. Pat. No. 4,822,543, issued Apr. 18, 1989 to Dean, et al.; U.S. Pat. No. 4,889,595, issued Dec. 26, 1989 to Schoggen, et al.; U.S. Pat. No. 4,898,642, issued Feb. 6, 1990 to Moore, et al.; and U.S. Pat. No. 4,935,022 issued Jun. 19, 1990 to Lash, et al. (It is understood, however, that cross-linked cellulose fibers are sufficiently modified that they may no longer be considered as either cellulosic, or as natural fibers, per se.)

The second group of fibers should also be of high compressive modulus and should maintain a relatively high modulus when wetted. The second group of fibers should also preferably be wet and dry resilient. Suitable fibers include, but are not limited to synthetic fibers comprised of polyester, polypropylene, polyethylene, nylon, viscous rayon fibers, or cellulose acetate, with polyester fibers being preferred.

The fibers in the second group of fibers are preferably longer than the fibers in the first group of fibers. Preferably, the fibers in the second group of fibers are greater than or equal to about ¼ inch (about 0.6 cm.) long, and are more preferably greater than or equal to about ½ inch (about 1.3 cm.) long. The denier of the fibers in the second group of fibers are preferably greater than the denier of the fibers in the first group of fibers. The fibers in the second group of fibers preferably have a denier per filament of between about 6 and about 40. More preferably, the denier is between about 15 and about 30, and most preferably between about 15 and about 25.

The fibers in the second group of fibers may be hydrophilic, hydrophobic, or partially hydrophilic and partially hydrophobic. The fibers in the second group of fibers preferably have at least some hydrophilic component (preferably a cellulosic component). The fibers in the second group of fibers can be provided with a hydrophilic component in a number of suitable ways. These include, but are not limited to coating or treating the fibers to render them, or at least their surfaces, hydrophilic.

One suitable type of synthetic fibers for use in the second group of fibers are crimped polyester fibers. Suitable synthetic fibers are available from Eastman Kodak Textile Fibers Division Kingsport, Tenn. as the KODEL 200 and 400 Series. One suitable type of synthetic fiber is the KODEL 410 fiber. A suitable polyester fiber is the KODEL 431 fiber. These KODEL fibers are preferably crimped at a crimping frequency of between about 5 and 7, preferably about 6, more preferably 6.3 crimps per linear inch (i.e., per 2.5 cm.). The fibers are preferably crimped at a crimping angle of between about 70° to about 91°, preferably about 88°. Crimping provides the fibers with improved resilience, among other desired properties. The fibers have a denier of 15 per filament and a length of about 0.5 inch (about 1.3 cm.). They may be coated with a hydrophilic or hydrophobic finish by any suitable method known in the art.

In an alternative embodiment, it is possible to replace the cellulose fibers in the first group of fibers with very short, low denier, synthetic fibers (with hydrophilic surfaces). The blended core 38 in this situation would consist of short, low denier, hydrophilic first group of synthetic fibers (such as polyester fibers with a CELWET finish) and long, high denier second group of synthetic fibers.

Such a blended core may also contain particles of hydrogel-forming polymer gelling agents to increase the absorptive capacity of the core.

In one preferred embodiment, the hydrogel-forming polymer gelling agents comprise "high-speed" absorbent gelling materials. The term "high-speed" absorbent gelling materials, as used herein, means those absorbent gelling materials that are capable of absorbing exudates at such a rate that they reach at least about 40%, preferably at least about 50%, and most preferably at least about 90% of their capacity in less than or equal to about 10 seconds. A suitable method for measuring the percent rate of capacity is described in U.S. patent application Ser. Nos. 07/637,090 and 07/637,571 filed by Noel, et al. and Feist, et al. In alternative embodiments, it is also possible for the high-speed absorbent gelling materials to be mixed with other types (or ordinary speed) absorbent gelling materials.

Preferably, in the embodiment described immediately above, the high-speed absorbent gelling materials are in fibrous form. Such fibers (though not necessarily high-speed fibrous absorbent gelling materials) are discussed more fully in U.S. Pat. No. 4,855,179, issued Aug. 8, 1989, to Bourland, et al. The term "fibrous absorbent gelling materials", as used herein, is intended to include absorbent gelling materials in the form of fibers that are comprised entirely of absorbent gelling material and bi-component fibers that are comprised at least partially of other materials which have their surfaces coated with absorbent gelling materials. A suitable fibrous high speed absorbent gelling material is known as FIBER-SORB SA7000 formerly manufactured by Arco Chemical Company of Newton Square, Pa.

The effective utilization of hydrogel-forming polymer gelling agents is believed to be improved in such a blended core. The use of higher concentrations of hydrogel-forming polymer gelling agents may also be possible.

The blended absorbent core 38 is preferably compressed to a density of at least about 1.5 g/cubic inch (about 0.09 g/cm$^3$). The blended core 42 may be compressed to densities at least as high as about 4.0 g/cubic inch (about 0.25 g/cm$^3$) to improve fluid wicking while still maintaining good softness and flexibility. (The density values specified above do not include the weight of any particles of absorbent gelling material.) Densification may be applied to the entire absorbent core 38 or only to selected portions. Patterned densification allows tailoring of the fluid handling properties to a specific need. For example, the density may be very low in the fluid target area to maximize fluid acquisition speed, and density may be very high near the core edges to maximize fluid wicking.

In one particularly preferred embodiment, the improved absorbent core 38 is an air-laid blend comprised of approximately 15% of 0.5 inch long, 15 denier per filament crimped polyester fibers and approximately 85% of cross-linked cellulose fibers compressed to a density of about 1 g/cubic inch (about 0.06 g/cm$^3$).

The blended absorbent core 38 can be used as the entire core or it can be used as one or more layers in a layered construction.

In a layered construction, one or more layers can consist of all cellulose or cellulose/hydrogel-forming polymer material blends. The layers could also have differing fiber and/or absorbent gelling material content. For example, a higher percentage of absorbent gelling material could be provided in the lower layers to provide additional liquid storage capacity.

The backsheet 36 is impervious to liquids and, thus, prevents menstrual fluid from soiling the clothing of the user. Any material used in the art for such purpose can be utilized herein. Suitable materials include embossed or non-embossed polyethylene films and laminated tissue. A suitable polyethylene film is manufactured by Monsanto Chemical Corporation and marketed in the trade as Film No. 8020.

A particularly preferred extensible backsheet 36 is an extended adhesive film Formula #198–338 manufactured by the Findley Adhesives Company of Wauwatosa, Wis. which is described in greater detail in the Capillary Channel Fiber patent applications.

The end edges of the topsheet 34 and backsheet 36, 34b and 36b, as shown in FIG. 1, preferably also extend beyond the end edges 38b of the absorbent core 38. The topsheet 34 and backsheet 36 are preferably joined at a seam 33 that extends around the entire periphery 30 of sanitary napkin 20. The seam 33 can be formed by any means commonly used in the art for this purpose such as by gluing, crimping, or heat-sealing. The embodiment shown is preferred for ease of construction. (In alternative embodiments, other means of uniting the various elements can be used.)

FIG. 2 also shows the fasteners (or attachment means), such as adhesive fastener 50, which is adapted to secure sanitary napkin 20 within the crotch region of an undergarment. As shown in FIG. 2, the adhesive fastener 50 may be in the form of two parallel longitudinally oriented strips of adhesive. FIG. 6 shows a preferred adhesive pattern comprising two rectangular adhesive patches and six square adhesive patches for use in an extensible sanitary napkin.

The adhesive patches 50 can be extensible, inextensible, or some patches can be extensible and some inextensible. Any adhesive or glue used in the art for such purpose can be used herein, with pressure-sensitive adhesive being preferred. Suitable adhesives are Century A-305-IV manufactured by the Century Adhesives Corporation and Instant LOK 34-2823 manufactured by National Starch Company. Suitable extensible adhesives are the adhesives on the Findley extended adhesive film backsheet material described above.

The fasteners 50 used with the present invention are not limited to adhesives. Any type of fastener used in the art can be used for such purpose. For example, the sanitary napkin 20 could be secured to the wearer's undergarment by mechanical fasteners, or by the fastener described in U.S. Pat. No. 4,946,527 entitled "Pressure-Sensitive Adhesive Fastener and Method of Making the Same" issued to Battrell on Aug. 7, 1990. For simplicity, however, the fasteners will be described in terms of adhesive attachment means.

The adhesive fasteners 50 are covered by a removable release liner 52. The pressure-sensitive adhesives should be covered with release liners 52 to keep the adhesives from sticking to extraneous surfaces prior to use. Any commercially available release liner commonly used for such purposes can be used herein. In one particularly preferred alternative embodiment, the release liner could be replaced by a wrapper that provides both an individually packaged sanitary napkin and a container for disposing the sanitary napkin after use, such as described in U.S. Pat. No. 4,556,146 issued to Swanson, et al. on Dec. 3, 1985.

In alternative embodiments, which should be capable of being understood by one skilled in the art without separately illustrating the same, particularly if the longitudinal side margins 40 are formed by an extension of the topsheet and backsheet beyond the longitudinal edges 38a of the core 38, the tucks 42 may be formed only in the topsheet or only in the backsheet, but not both. In such an alternative embodiment, the unpleated component is simply joined to the pleated component after the tuck is formed.

In another alternative embodiment, the topsheet 34 can be provided with a triangular notch above the desired tuck location. The tuck 42 is made only in the backsheet 36. The cut edges of the topsheet 34 can be brought together to form a butt or lap joint. This embodiment, and the embodiment described in the preceding paragraph provide the ability to make the longitudinal side margins 40 even thinner in the region of the tucks 42.

In other alternative embodiments, the longitudinal side margins 40 could be shortened by any of the ways for shortening the side flaps of a disposable diaper set forth in U.S. Pat. No. 3,807,402 issued to Miller, et al. on Apr. 30, 1974. However, the present invention is not intended to apply to diapers or the like which are drawn up between the legs having end regions that overlap and are fastened around the waist of the wearer. (The present invention is directed to those types of absorbent articles that are typically worn in and attached to the crotch portion of a garment, such as the wearer's usual undergarments.) In other alternative embodiments, the longitudinal side margins 40 could be shortened by any of the ways described in P&G UK Patent Application 2 168 253A.

The drawing figures merely provide some examples of suitable tuck configurations. Many other tuck configurations are also possible, and fall within the scope of the present invention.

In other alternative embodiments to any of those described previously, the tucks 42 could even be located in margins along the transverse end edges 30 of the sanitary napkin. This could be used to cause the end edges to stand up also, and provide a sanitary napkin with lateral curvature.

In still other alternative embodiments, the sanitary napkin could be provided with additional components. These could be positioned between the topsheet and the backsheet on either side of the absorbent core. For instance, the sanitary napkin could be provided with an acquisition layer or sheet such as that designated 54 in FIG. 6. Suitable acquisition sheets are described in greater detail in U.S. Pat. No. 5,009,653 issued to Osborn, the Capillary Channel Fiber patent applications, and in U.S. patent application Ser. No. 07/810,774 filed in the name of Cree, et al. Suitable capillary channel fibers (that is, fibers having channels formed therein, preferably, on their exterior surfaces). Such fibers are described in greater detail in EPO Patent Application 0 391,814 published Oct. 10, 1990.

The present invention, thus, provides an absorbent article which assumes a curved, body-conforming shape having sides that stand up to serve as barriers to the soiling of the wearer's undergarments without attaching elastics to the longitudinal side edges of the absorbent article. Because there are no elastics, the product maintains its curvature and the amount of curvature is not dependent on the thickness of the absorbent article. The product will also retain its curvature even in relatively thick products.

While a preferred absorbent article in the form of a sanitary napkin embodiment of the present invention has been described, numerous other absorbent articles could be provided with the tucks of the present invention. Some other absorbent articles in the form of sanitary napkins which could, in at least some embodiments, be provided with longitudinal side margins having tucks therein are disclosed in U.S. Pat. Nos. 4,950,264 and 5,009,653, both entitled "Thin, Flexible Sanitary Napkin" which issued to Osborn on Aug. 21, 1990 and Apr. 23, 1991, respectively.

Suitable absorbent articles in the form of panty liners that could be provided with the tucks described herein are disclosed in U.S. Pat. No. 4,738,676 issued to Thomas W. Osborn on Apr. 19, 1988.

Suitable absorbent articles, some of which are in the form of adult incontinence products, which could be provided with the tucks described herein, are disclosed in U.S. patent application Ser. No. 07/637,571 filed respectively by Noel, et al. and Feist, et al. on Jan. 3, 1991.

The disclosures of all patents, patent applications (and any patents which issue thereon as well as any corresponding published foreign patents or patent applications), and publications mentioned throughout this description are hereby incorporated by reference herein. It is expressly not admitted, however, that any of the documents incorporated by reference herein teach or disclose the present invention. It is also expressly not admitted that any of the commercially available products or materials described herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent article such as a sanitary napkin, panty liner, or adult incontinent article for wearing within the crotch portion of a garment and fastening to said garment, said absorbent article having two longitudinal side margins and two end edges, said absorbent article comprising:

a liquid pervious topsheet;

a liquid impervious backsheet joined to said topsheet; and an absorbent core positioned between said topsheet and said backsheet;

a fastener on said backsheet for fastening said absorbent article to said garment; wherein said topsheet, backsheet, and absorbent core each have two longitudinal edges and two transverse edges, and the longitudinal edges of said topsheet and backsheet extend outward beyond the longitudinal edges of said absorbent core to form said longitudinal side margins, said logitudinal side margins being disposed laterally outward of said longitudinal edges of said absorbent core, and at least one of the longitudinal side margins of the absorbent article has at least one tuck formed therein wherein a first portion of said at least one longitudinal side margin is folded as a unit adjacent to a second portion of said longitudinal side margin about a first fold line and said folded first and second portions are folded about a second fold line over a third portion of said longitudinal side margin, wherein said absorbent article is shaped into and maintained in a curved configuration wherein said end edges of said absorbent article are displaced upward only by said folded portions of said absorbent article disposed laterally outboard of said longitudinal edges of said absorbent core, said folded portions being permanently secured in a side by side relationship.

2. The absorbent article of claim 1 wherein each of said longitudinal side margins is provided with said at least one tuck.

3. A longitudinally extensible absorbent article according to claim 1 wherein said topsheet comprises an extensible liquid pervious topsheet; said backsheet comprises an extensible liquid impervious backsheet; and said absorbent core comprises an extensible absorbent core.

4. An absorbent article for wearing within the crotch portion of a garment, said absorbent article having two longitudinal side margins, said absorbent article comprising:

a liquid pervious topsheet, said topsheet having two longitudinal edges and two transverse edges;

a liquid impervious backsheet joined to said topsheet, said backsheet having two longitudinal edges and two transverse edges;

an absorbent core positioned between said topsheet and said backsheet, said absorbent core having two longitudinal edges and two transverse edges;

said longitudinal edges of said topsheet and backsheet extending beyond the longitudinal edges of said absorbent core to form said longitudinal side margins, wherein at least one of the longitudinal edges of said topsheet has a notch formed therein wherein the portions of said topsheet surrounding said notch comprise surrounding portions, and said notch has two sides defined by the surrounding portions of said topsheet, and said sides are secured together, and the longitudinal side edges of the backsheet underlying said notch has at least one tuck formed therein, and said longitudinal edges of said topsheet and backsheet are secured together.

* * * * *